US008369480B2

(12) United States Patent
Barty

(10) Patent No.: US 8,369,480 B2
(45) Date of Patent: Feb. 5, 2013

(54) DUAL ISOTOPE NOTCH OBSERVER FOR ISOTOPE IDENTIFICATION, ASSAY AND IMAGING WITH MONO-ENERGETIC GAMMA-RAY SOURCES

(75) Inventor: Christopher P. J. Barty, Hayward, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 850 days.

(21) Appl. No.: 12/506,639

(22) Filed: Jul. 21, 2009

(65) Prior Publication Data

US 2013/0003924 A1    Jan. 3, 2013

Related U.S. Application Data

(63) Continuation-in-part of application No. 11/528,182, filed on Sep. 26, 2006, now Pat. No. 7,564,241.

(60) Provisional application No. 60/720,965, filed on Sep. 26, 2005.

(51) Int. Cl.
*G01N 23/04*    (2006.01)

(52) U.S. Cl. ........................................................ 378/57

(58) Field of Classification Search .................... 378/57, 378/62, 87
See application file for complete search history.

(56) References Cited

U.S. PATENT DOCUMENTS

| 3,780,294 A | 12/1973 | Sowerby |
|---|---|---|
| 5,040,200 A | 8/1991 | Ettinger et al. |
| 5,115,459 A | 5/1992 | Bertozzi |
| 5,293,414 A | 3/1994 | Ettinger et al. |
| 5,323,004 A | 6/1994 | Ettinger et al. |
| 5,420,905 A | 5/1995 | Bertozzi |
| 6,442,233 B1 | 8/2002 | Grodzins et al. |
| 6,661,818 B1 | 12/2003 | Feldman et al. |
| 6,684,010 B1 | 1/2004 | Morris et al. |
| 7,060,983 B2 | 6/2006 | Tumer |
| 7,120,226 B2 | 10/2006 | Ledoux et al. |
| 7,693,262 B2 | 4/2010 | Bertozzi et al. |
| 2004/0109532 A1 | 6/2004 | Ford et al. |
| 2005/0179911 A1 | 8/2005 | Boomgarden et al. |
| 2006/0166144 A1 | 7/2006 | Kolste et al. |
| 2006/0188060 A1 | 8/2006 | Bertozzi et al. |
| 2007/0263767 A1 | 11/2007 | Brondo |

FOREIGN PATENT DOCUMENTS

| WO | 2005081017 | 1/2005 |
|---|---|---|
| WO | 2007038527 | 5/2007 |
| WO | 2009097052 | 8/2009 |
| WO | 2009086503 | 9/2009 |

OTHER PUBLICATIONS

C. A. Hagmann, et al., "Transmission-based detection of nuclides with nuclear resonance fluorescence using a quasimonoenergetic photon source", J. Appl. Phys., vol. 106 (Oct., 2009), pp. 084901.

*Primary Examiner* — Courtney Thomas
(74) *Attorney, Agent, or Firm* — John P. Wooldridge

(57) ABSTRACT

A dual isotope notch observer for isotope identification, assay and imaging with mono-energetic gamma-ray sources includes a detector arrangement consists of three detectors downstream from the object under observation. The latter detector, which operates as a beam monitor, is an integrating detector that monitors the total beam power arriving at its surface. The first detector and the middle detector each include an integrating detector surrounding a foil. The foils of these two detectors are made of the same atomic material, but each foil is a different isotope, e.g., the first foil may comprise U235 and second foil may comprise U238. The integrating detectors surrounding these pieces of foil measure the total power scattered from the foil and can be similar in composition to the final beam monitor. Non-resonant photons will, after calibration, scatter equally from both foils.

29 Claims, 9 Drawing Sheets

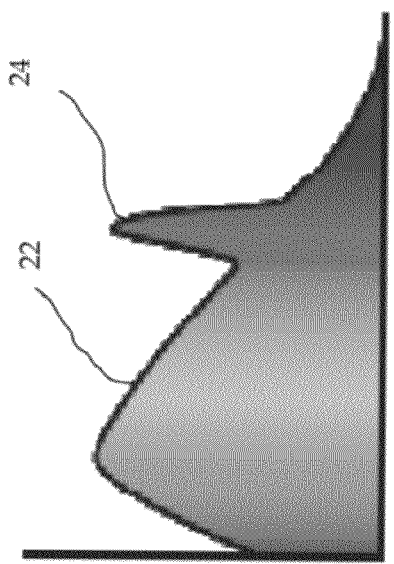
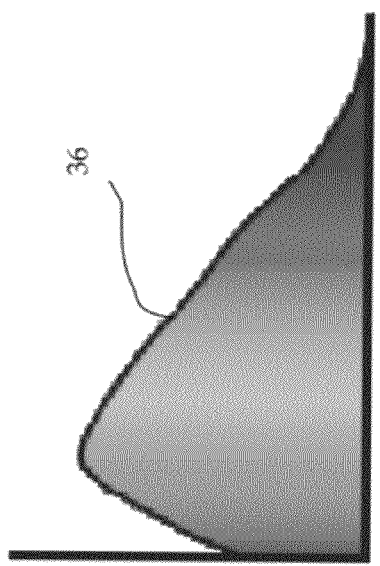
Figure 1B
Figure 2B

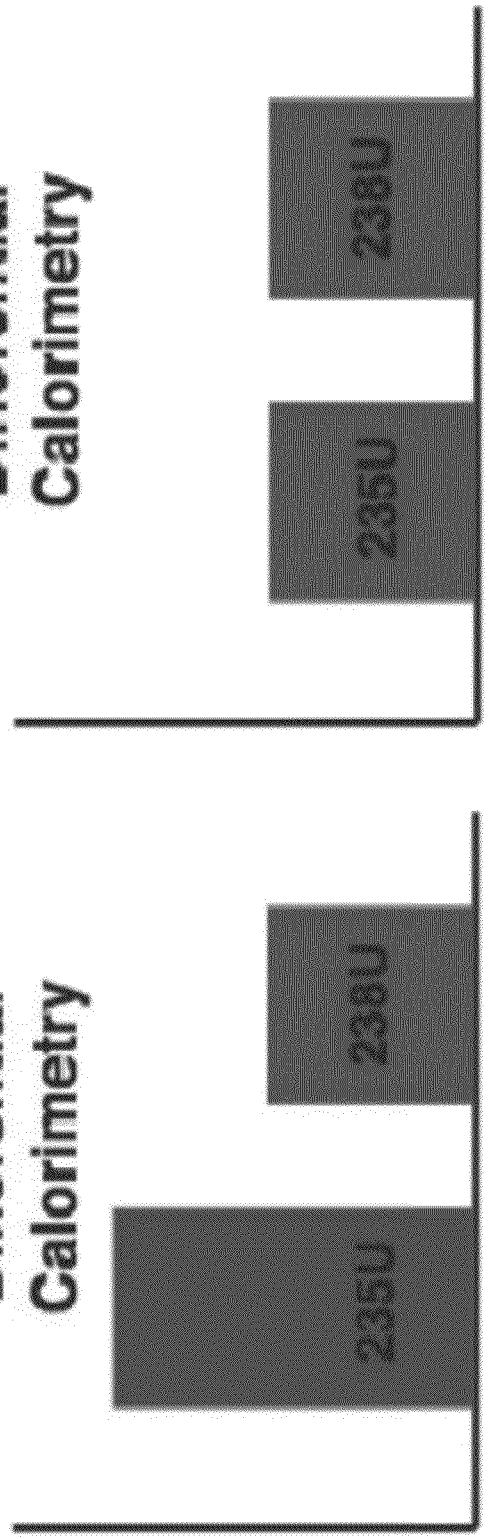

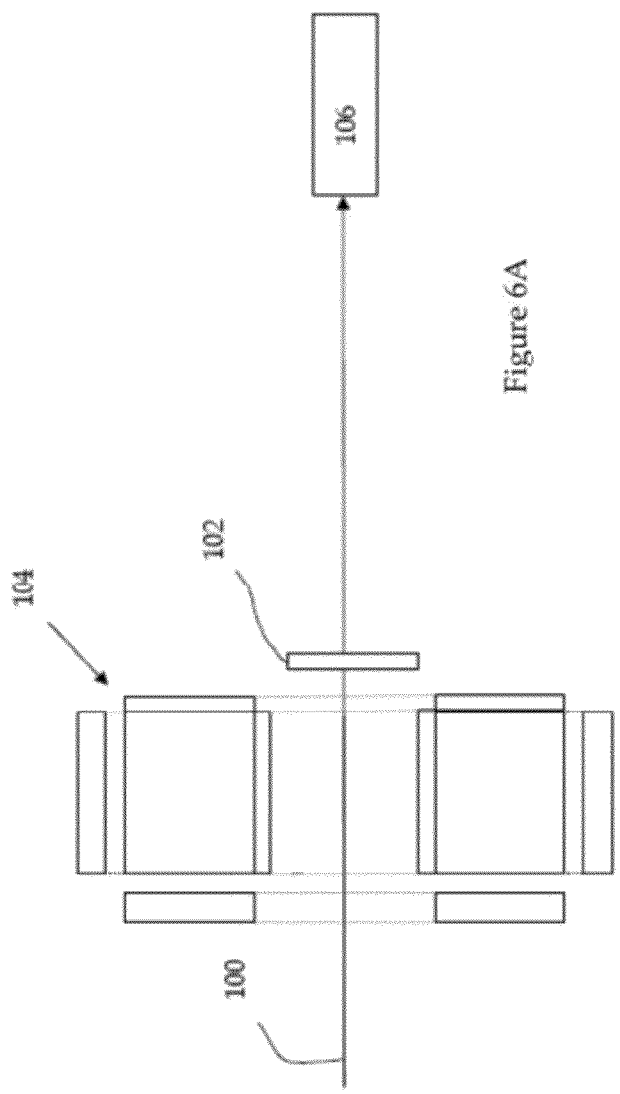

DUAL ISOTOPE NOTCH OBSERVER FOR ISOTOPE IDENTIFICATION, ASSAY AND IMAGING WITH MONO-ENERGETIC GAMMA-RAY SOURCES

This application is a continuation-in-part of U.S. patent application Ser. No. 11/528,182, filed Sep. 26, 2006, incorporated herein by reference, which claims priority to U.S. Provisional Application No. 60/720,965, filed Sep. 26, 2005.

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to applications utilizing mono-energetic gamma-rays (MEGa-rays), and more specifically, it relates to techniques that utilize MEGa-rays for characterizing isotopes.

2. Description of Related Art

MEGa-ray sources are created by the scattering of energetic (Joule-class), short-duration (few picosecond) laser pulses off of relativistic electron beams (several hundred MeV). The resulting scattered photons are forwardly directed in a narrow beam (typically milli-radians in divergence), are mono-energetic, tunable, polarized and have peak photon brilliance (photons/second/unit solid angle, per unit area, per unit bandwidth) that exceeds that of the best synchrotrons by over 15 orders of magnitude at gamma-ray energies in excess of 1 MeV. Such beams can efficiently excite the protons in the nucleus of a specific isotope, so called nuclear resonance fluorescence (NRF). NRF resonant energies are a function of the number of protons and neutrons in the nucleus and are thus a unique signature of each isotope. It has been suggested that NRF can be used to identify specific isotopes. It is has been further suggested (T-REX/FINDER) that MEGa-ray sources are ideal for this application and not only enable identification of isotopes but can also be used to determine the quantity and spatial distribution of isotopes in a given object. In order to accomplish these tasks one analyzes the MEGa-ray beam transmitted through a particular object. NRF resonances are narrow, typically 10E-6 wide compared to the resonant energy, e.g., 1 eV wide for a 1 MeV resonant energy. MEGa-ray sources on the other hand are typically 10E-3 wide relative to their carrier energy, e.g., 1 keV wide for a carrier energy of 1 MeV. A given amount of (e.g., grams) of a resonant isotope removes a corresponding amount of resonant photons from a MEGa-ray beam, according to Beer's law. Detection or measurement of the absence of resonant photons in a MEGa-ray beam transmitted through an object can be thus be used to determine not only the presence of the material but also its location and its quantity. To do so requires a detector capable of resolving the number of resonant photons removed by the desired object from the MEGa-ray beans. Known gamma-ray spectroscopy technologies are not capable of resolutions better than 10E-3 in the MeV spectral region and are thus not able to accomplish the task. One method suggested by Bertozzi et al. (Bertozzi patent) envisions using a piece of the material under observation after the object in question to evaluate the removal of NRF resonant photons from the beam.

Let us consider in some detail the Bertozzi suggestion using a specific example, namely the location of U235 hidden within a large container such as that used for a trans-oceanic commerce. The Bertozzi suggestion applies specifically to interrogation with a polychromatic gamma-ray beam such as that produced by a Bremsstrahlung source. Referring to FIG. 1A, in his suggestion, the beam 10 transmitted through the cargo container 12 impinges upon two "detectors". Transmission detector 14 is an energy collector that measures the total, gamma-rays passing through the object and the first detector 16, which consists of a piece (typically a foil) of the material/isotope that is being sought in the container, i.e., a foil 18 of U235 in this example. The foil of U235 in detector 16 is surrounded by a large area, gamma-ray spectrometer 20 that measures the spectrum of the photons scattered by the U235 foil 18. If U235 is present in the cargo container in quantities greater than a few grams, then the resonant photons will be removed from the interrogating gamma-ray beam and the gamma-ray spectrometer surrounding the foil of U235 will not see any resonant photons. As depicted in FIG. 1B, light scattered by the interrogating foil will consist of non-NRF photons and particles 22 such as Compton scattered photons, Delbruck photons and miscellaneous energetic particles. When beam 10 does not propagate onto any U235 within the container, then in addition to the non-NRF photons and particles, spectroscopy of the scattered light will reveal NRF photons 24. FIG. 2A shows a cargo container 30, that includes U235 material 32 that is interrogated by a polychromatic beam 34 that includes light resonant at the U235 line. As shown in FIG. 2B, spectroscopy of the scattered light shows only non-NRF photons and particles 36 and thereby reveals the absence of NRF photons and thus the presence of U235 material in the container. While this method in principle works, it has some significant limitations, in particular, it requires gamma-ray spectroscopy of the scattered photons to be effective. Gamma-ray spectroscopy is difficult and is accomplished in nearly all cases by collecting one gamma-ray at a time and analyzing the total energy of that photon. This can work for beams that have photons distributed evenly in time, e.g., those coming from a Bremsstrahlung source. However Bremsstrahlung sources have been shown to be ill-suited for transmission based NRF detection schemes due to their wide bandwidth and beam divergence which are both ill-matched to NRF detection requirements (Fruit et al. paper). MEGa-ray beams are well suited to transmission detection due to their narrow bandwidth and low divergence (100× smaller than Bremsstrahlung); however, these sources by their nature produce large bursts of photons, up to 10E10 per pulse at rates of 10's to 100's of times per second. MEGa-ray sources are ill-matched to single photon counting based gamma-ray spectroscopy.

Alternative methods that eliminate the limitations of the Bertozzi method are desirable.

SUMMARY OF THE INVENTION

It is an object of the present invention to enable the efficient detection, assay and imaging of isotopes via nuclear resonance fluorescence (NRF) excited by laser-based, inverse-Compton scattering sources of mono-energetic gamma-rays (MEGa-rays).

This and other objects will be apparent based on the disclosure herein.

Embodiments of the present invention alleviate the need for single photon counting spectroscopy with MEGa-ray based detection arrangements. FIG. 3A shows an embodiment of the present invention including a detector arrangement that consists not of two detectors downstream from the object under observation but instead three. The latter detector, which operates as a beam monitor, is an integrating detector that monitors the total beam power arriving at its surface. This transmission detector can, e.g., be identical to the latter detector in the Bertozzi scheme, which is described in U.S. 2006/0188060 A1, incorporated herein by reference. The first detector and the middle detector each include an integrating detector surrounding a foil. The foils of these two detectors are made of the same atomic material, but each foil is a different isotope, e.g., the first foil may comprise U235 and second foil may comprise U238. The integrating detectors surrounding these pieces of foil measure the total power scattered from the foil and can be similar in composition to the final beam monitor. Non-resonant photons will, after calibration, scatter equally from both foils, i.e., Compton, Delbruck, etc., and are not, to first order, dependent upon the number of nucleons in the isotope but are a function of the atomic element. As shown in FIG. 3B, if the object under interrogation has no U235 present and the interrogating MEGa-ray beam is tuned to the U235 resonant transition, then the first foil will produce resonant photons as well as the non-resonant photons and scatter and thus more energy will emanate from the first foil than the second foil. A variety of methods for diagnosing the content of an interrogated object are provided herein and are within the scope of the present invention. For example, the ratio of the energy scattered by each foil or the difference in energy scattered by each foil can be used to determine not only the presence of the material in the object under interrogation, but the exact ratio or difference is a function of the amount of material present, thus this detector arrangement can also provide quantitative assay information. By arranging the foils in small pixels it is also possible to use MEGa-ray beams and NRF to determine with high spatial resolution (microns) the location of specific isotopes.

This generic arrangement is referred to as a Dual Isotope Notch Observer (DINO) since it effectively identifies the depth of the 10E-6 wide notch in the 10RE-3 wide transmitted MEGa-ray beam. Since MEGa-ray sources are new (only a couple of years old), no one ever needed to consider how to make a DINO like detector. A number of DINO configurations are within the scope of the present invention, including but not limited to:

a) sequential foils in which the attenuation of the first foil is calibrated and taken as part of the measurement;

b) a rotating foil arrangement in which the two (or more) foils are alternatively placed in the beam on sequential MEGa-ray pulses;

c) multiple arrangements of isotopes used with dual or multicolor MEGa-ray beams to detect and assay more than one isotope simultaneously;

d) detection and assay determined by the ratio of signals from both foils and the beam monitor;

e) detection and assay determined by the difference of signals from both foils and the beam monitor; and f) no beam monitor used but only the scattering from the isotopes is used to determine the presence and amount of material.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1B illustrates light scattered by an interrogating foil.

FIG. 2B illustrates a spectrum of scattered light showing only non-NRF photons and particles.

FIG. 3B shows that for an object under interrogation that has no U235 present and the interrogating MEGa-ray beam is tuned to the U235 resonant transition, then the foil will produce resonant photons as well as the non-resonant photons and scatter and thus more energy will emanate from the first foil than the second foil.

FIG. 4B shows that for an object under investigation that includes U235 and the interrogating MEGa-ray beam is tuned to the U235 resonant transition, resonant photons are removed from the beam, resulting in substantially similar energy levels emanating from first and second foils.

FIG. 6A illustrates an embodiment that uses a single rotating foil.

FIG. 6B shows the two halves of the rotating foil of FIG. 6A.

DETAILED DESCRIPTION OF THE INVENTION

Figure 1A:
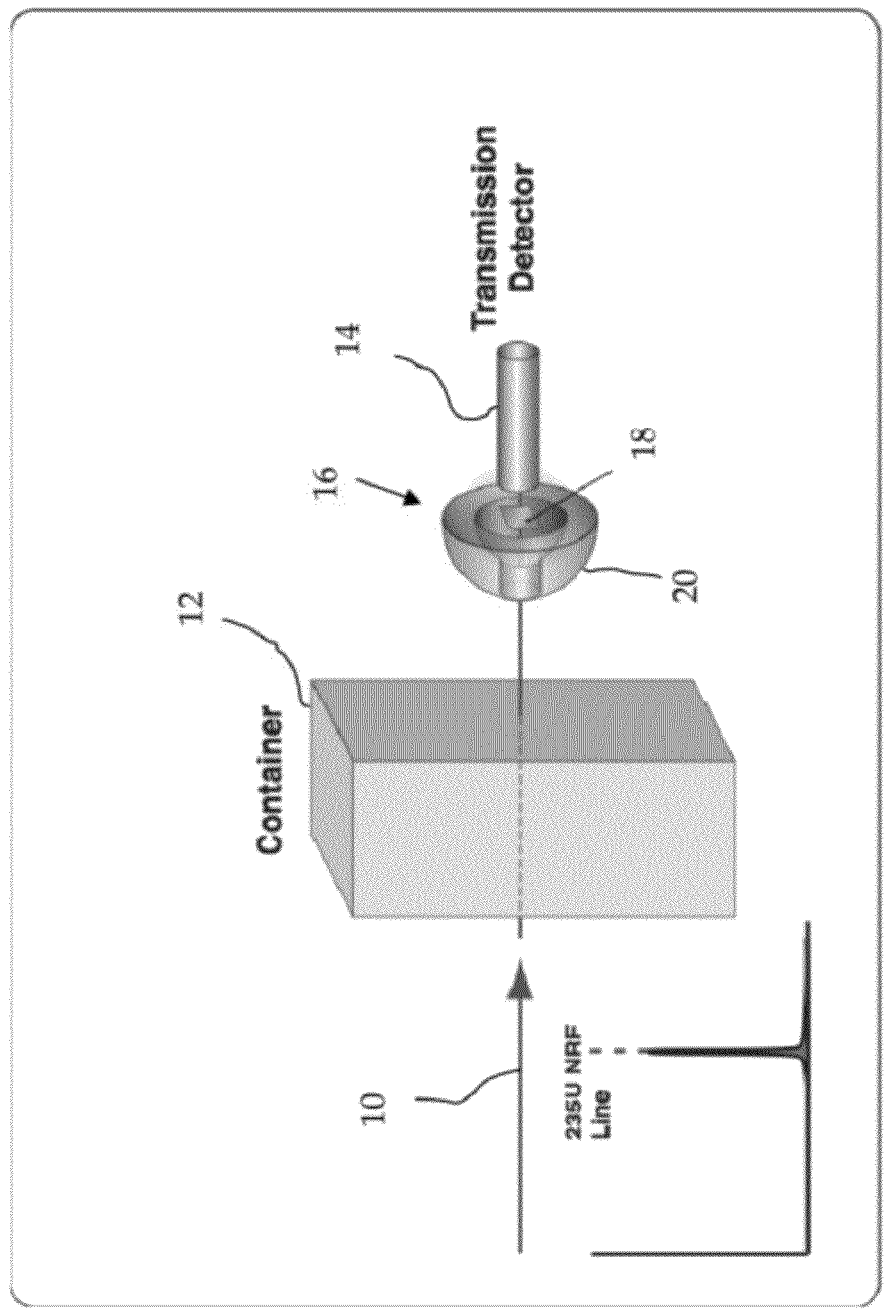
FIG. 1A shows a prior art configuration in which a beam transmitted through a cargo container impinges upon two detectors.
Figure 2A:
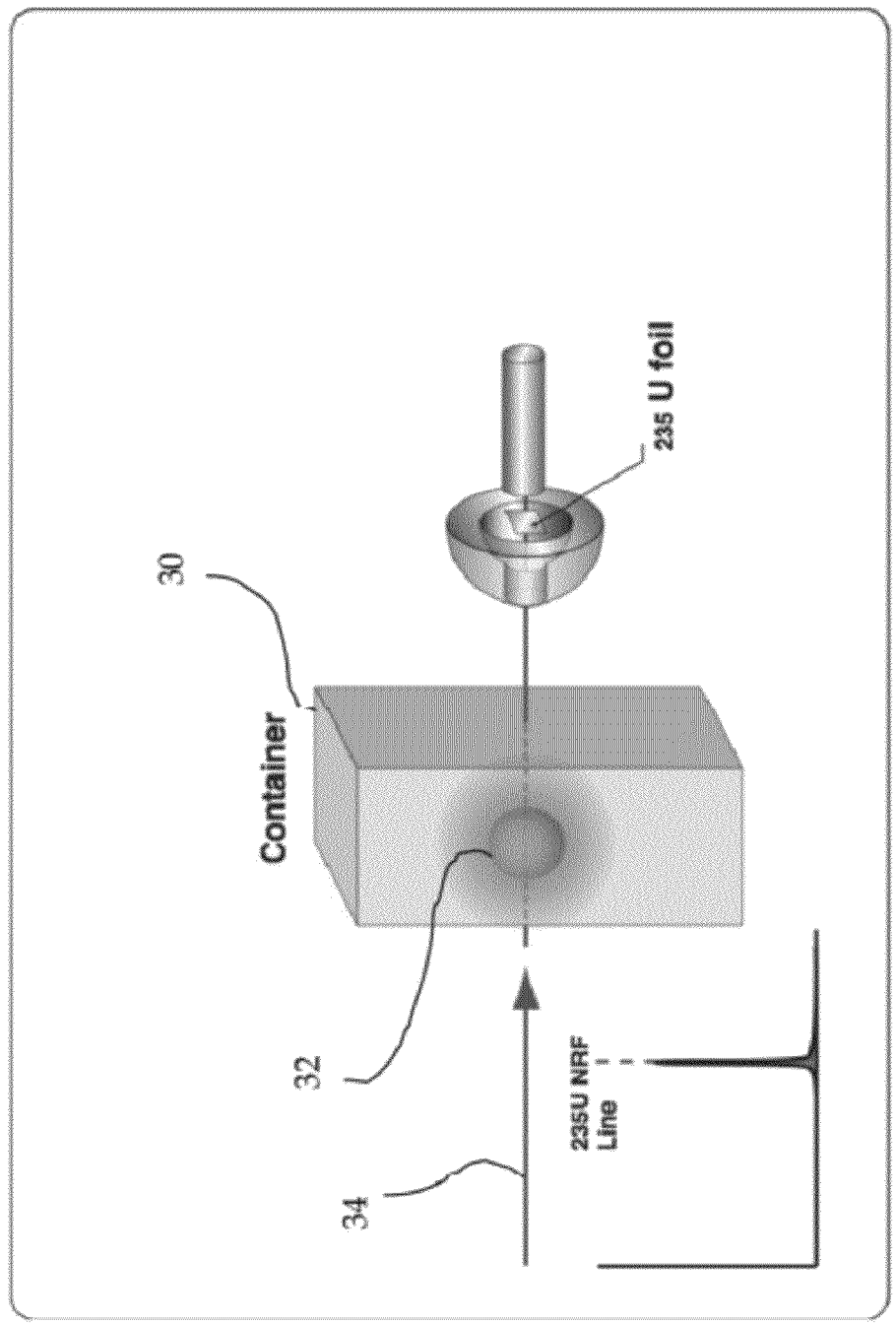
FIG. 2A shows a cargo container that includes U235 material that is interrogated by a polychromatic beam that includes light resonant at the U235 line.
Figure 3A:
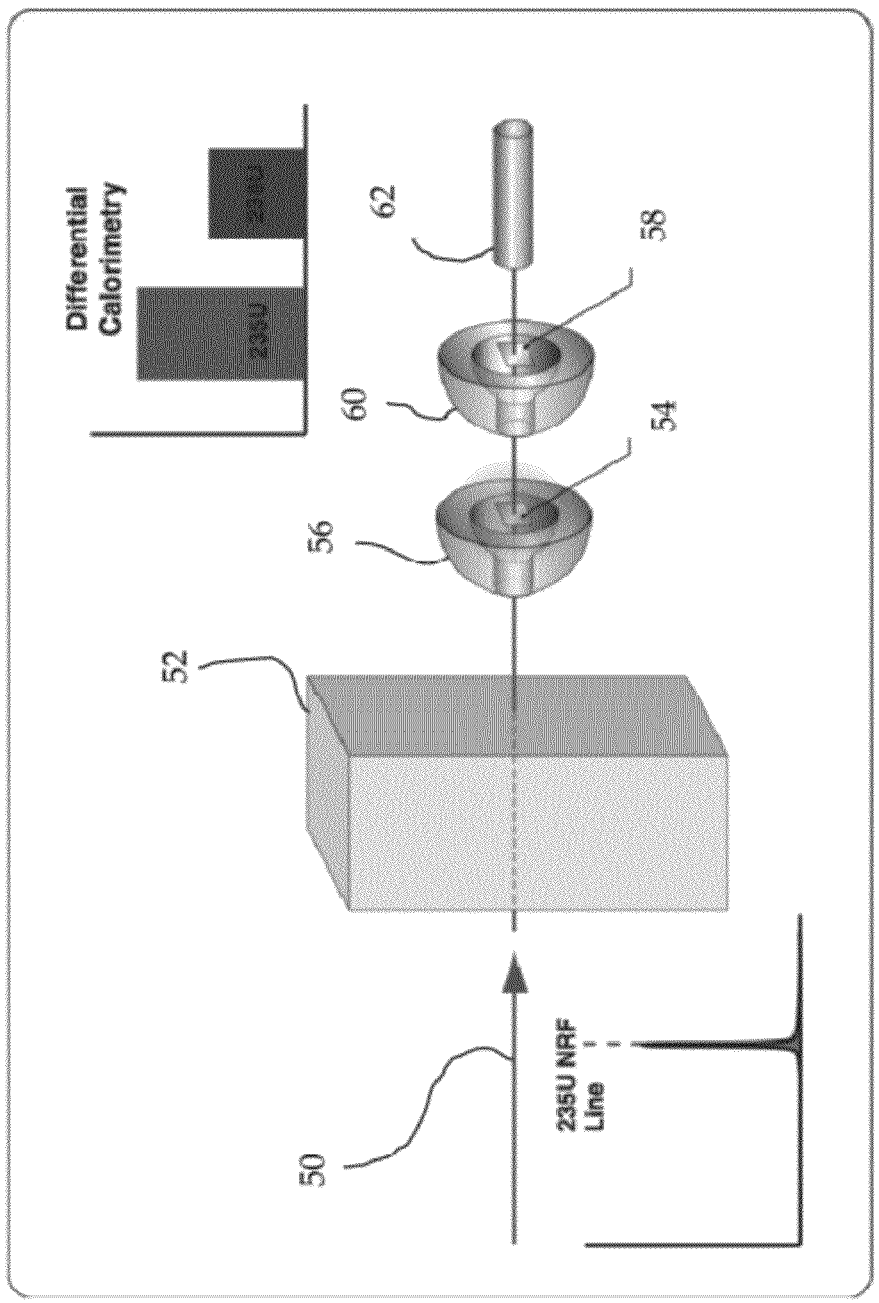
FIG. 3A shows an embodiment of the present invention including a detector arrangement that consists of three detectors downstream from a container having no U235 in the beam path.
Figure 4A:
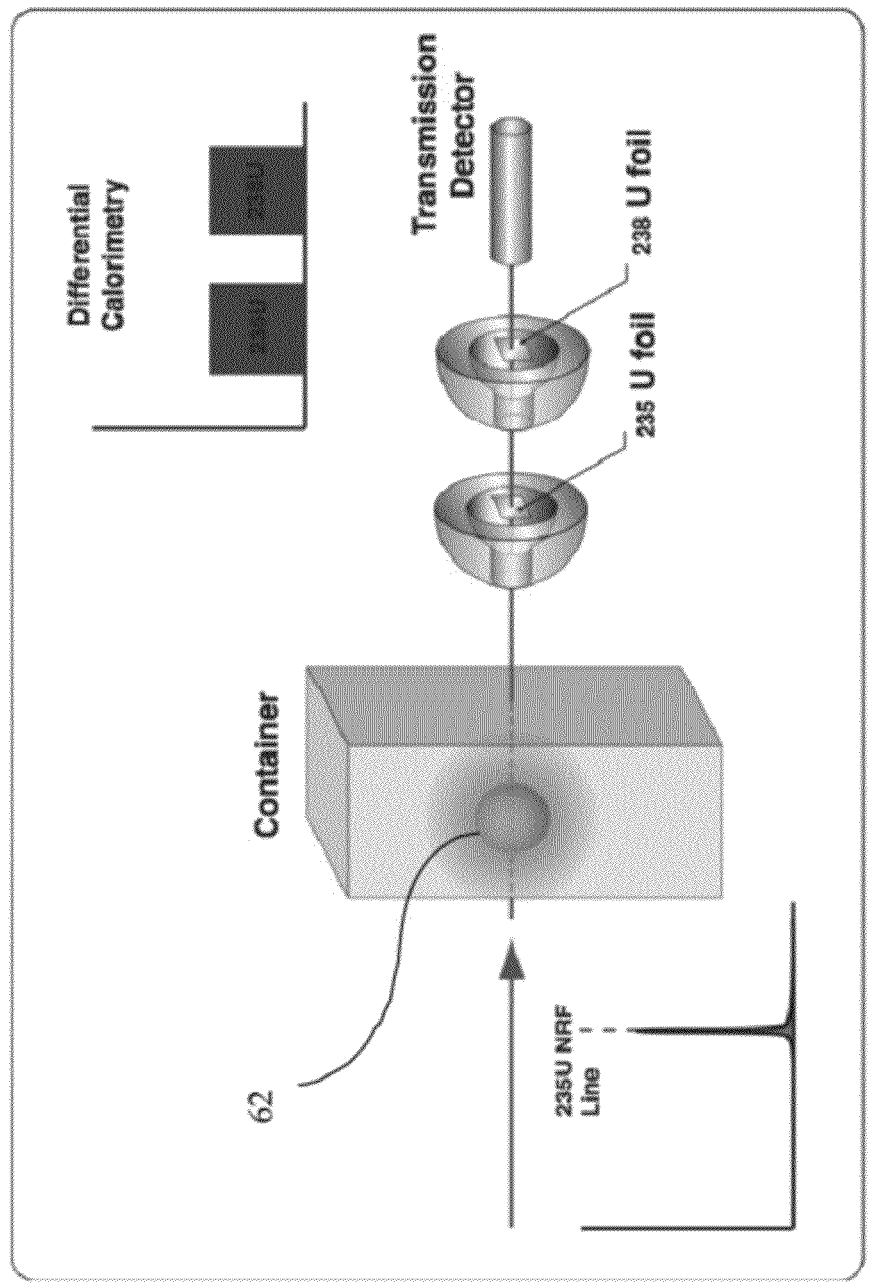
FIG. 4A shows an embodiment of the present invention including a detector arrangement that consists of three detectors downstream from a container having U235 in the beam path.

FIG. 3A shows an embodiment of the present invention where there is no U235 or U238 in the path of the beam. Specifically, MEGa-ray probe beam 50 is tuned at a U235 NRF line. The path of beam 50 as it traverses container 52, does not intersect any U235 or U238 material. After passing though container 52, beam 50 propagates to and through a first foil 54, which is surrounded by an integrating detector 56. After passing through foil 54, beam 50 propagates to and through a second foil 58, which is surrounded by an integrating detector 60. After passing through foil 58, beam 50 propagates onto an integrating detector 62. Since beam 50, which is tuned at the U235 NRF line, does not encounter any U235 as it passes through container 52, there is no reduction of U235 resonant photons within beam 50. Therefore, U235 foil 54 produces a larger amount of NRF than it would have if beam 50 had encountered U235 in its path through container 52. If a sufficient quantity of U235 had been present in the path of beam 50 within container 52, such that all of the resonant photons in beam 50 had been removed, then, after normalization of the signals at each detector to account for attenuation losses, the amount of non-resonant photons and scatter from foils 54 and 58 would have, to first order, been the same. In the example of FIG. 3A, there is no U235 (or U238) within the beam path through the container, and therefore, in addition to the non-resonant photons and scattered particles, the integrating detector collects resonance produced by the interaction of probe beam 50 with the U235 in foil 54. FIG. 3B depicts the signals produced by integrating detectors 56 and 58 in the example of FIG. 3A. The elements of FIG. 4A are identical in all respects to those of FIG. 3A, except that a quantity of U235 material 62 is in the path of beam 50 as it passes through container 52. In this example, the amount of U235 is sufficient to remove all of the resonant photons from beam 50, such that there is no production of U235 NRF from foil 54, as depicted in FIG. 4B. When absolutely no U235 NRF is produced by foil 54, the quantity of U235 within the beam path cannot be surmised. Due to the magnitude of gamma-ray energies (in excess of 1 MeV) produced by the MEGa-ray sources used in the present invention, as disclosed, e.g., in application Ser. No. 11/528,182 (U.S. Pat. No. 7,564,241), incorporated herein by reference, the present invention is capable of producing U235 NRF in foil 54 even in the presence of U235 within the path of beam 50 through container 52. Thus, if the amount of U235 NRF produced by foil 54 is less than that produced when beam 50 encounters no U235 in its path through container 54, the amount of U235 that is produced is indicative of the quantity of that material in the path of beam 50. Further, by moving the path of beam 50 relative to container 52, an image, both 2D and 3D, can be obtained of the U235 material within container 52. Other techniques for obtaining a 2D and 3D image are discussed below, and still others will be apparent to those skilled in the art based on the descriptions herein. Although the present invention uses examples for determining the presence, assay and image of U235, the present invention can be used for the same purposes in applications with other materials.

Figure 5:
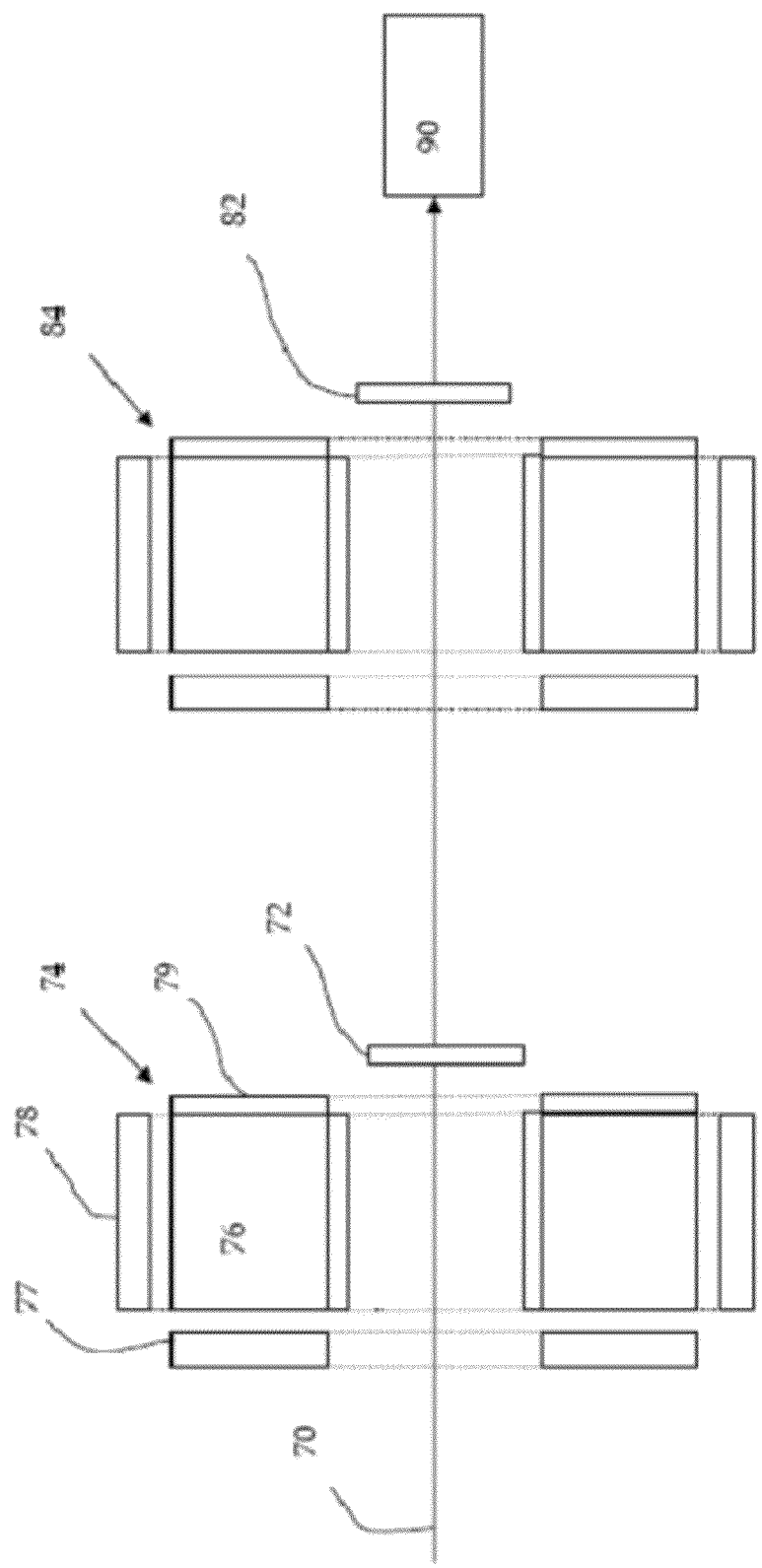
FIG. 5 illustrates an example of the invention where, after exiting an object under test, a probe beam passes through a U238 foil and then through a U235 foil before propagating onto the beam monitoring detector.

FIG. 5 illustrates another example where, after exiting an object under test (not shown), a probe beam 70, passes through U238 foil 72 and then through U235 foil 82 before propagating onto the beam monitoring detector 90. The integrating detector 74, shown in cross-section, positioned near foil 72, is substantially similar, in this example, to the detector 84 positioned near foil 82. Integrating detector 74 is formed of a scintillator 76 and two photomultipliers 77 and 78. A Compton shield 79 is positioned between foil 72 and scintillator 76.

FIG. 6A illustrates an embodiment that uses a single rotating foil rather that the dual foils described supra. In this example, after exiting a test object, MEGa-ray beam 100 passes through rotating foil 102 and impinges on the integrating detector 106. An integrating detector 104, similar to the detectors 74 and 84 of FIG. 5, is located near rotating foil 102. FIG. 6B shows a front view of the rotating foil 102. As shown in FIG. 6B, one half 102' of the rotating foil comprises U235 and the other half 102" comprises U238. The beam 100 is pulsed at a fixed rate and the rotating foil 102 rotates at a fixed rate that is one half of the rate of pulses if beam 100. At such a rotational rate, the beam 100 will pass through the U235 portion in one pulse and in the next pulse, beam 100 will pass through the U238 portion.

Figure 7:
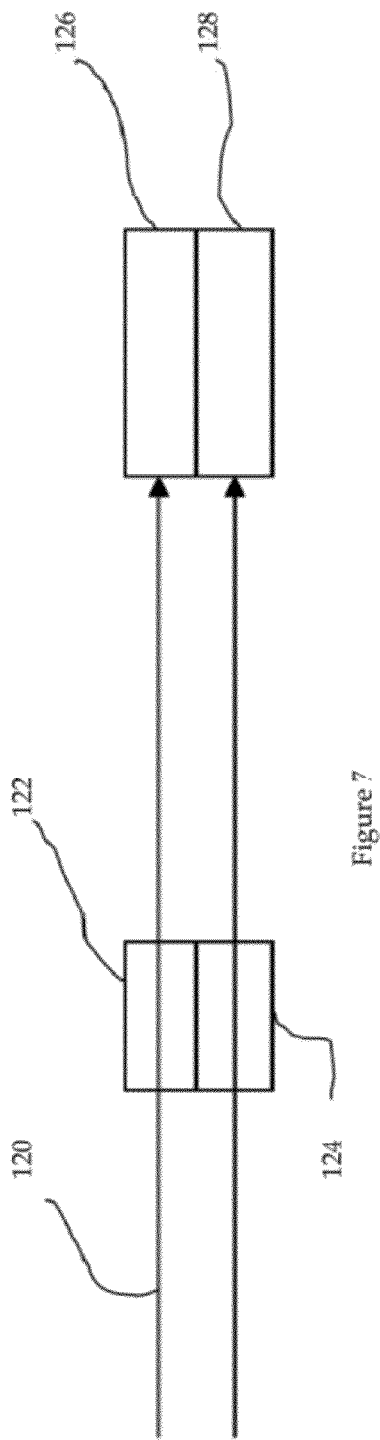
FIG. 7 is an example where a portion of a finite area MEGa-ray beam simultaneously passes through a U235 piece and a U238.

FIG. 7 is an example where a portion of a finite area MEGa-ray beam 120 simultaneously passes through U235 piece 122 and U238 piece 124. The portion of beam 120 that passes through U235 piece 122 propagates onto integrating detector 126 and the portion of beam 120 that passes through U238 piece 124 propagates onto integrating detector 128.

Figure 8:
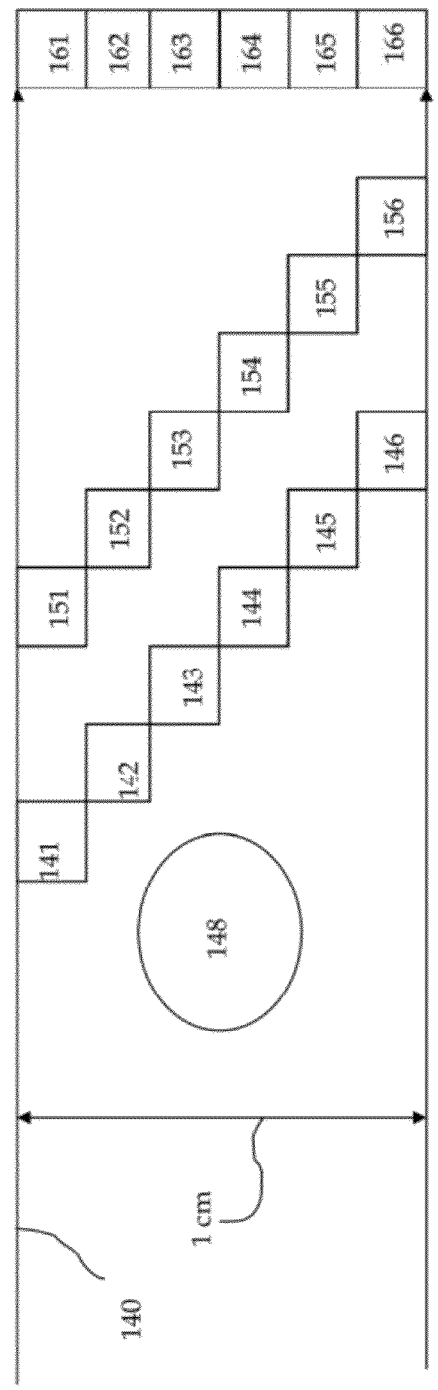
FIG. 8 illustrates a finite area MEGa-ray beam that propagates through pixels of U235 material in line with pixels of U238 material.

FIG. 8 illustrates a finite area MEGa-ray beam 140 that propagates through pixels 141-146 of U235 material in line with pixels 151-156 of U238 material. This beam will completely cover any U235 material that has a diameter of less than the beam diameter. For example, if the beam diameter 140' is 1 cm and a U235 piece 148 has a diameter of 0.5 cm, then U235 piece 148 will be completely covered by beam 140. A separate integrating detector (not shown) is positioned to measure U235 NRF and non-resonant photons and particles for each of pixels 141-146 of U235 material and pixels 151-156 of U238 material. In this example, a separate integrating detector of integrating detectors 161-166 is positioned to measure the beam portion that passes through each pixel pair. Thus, the portion of beam 140 that passes through pixel 141 will then pass through pixel 151 and will propagate onto integrating detector 161. Note that although pixels 141-146 and pixels 151-156 are depicted as a two dimensional array, each pixel can be a part of an array of pixels extending perpendicular to the plane of the page to create a three dimensional pixel array. This exemplary configuration instantly provides a complete 2 dimensional image of any piece of U235 that is smaller than the diameter of beam 140. Such a beam can be moved relative to a larger piece of U235 to obtain an image of such piece. The beam and the piece of U235 can be moved relative to one another to obtain a 3 dimensional image of the U235. The beam and its alignment to the pixel arrays can be held constant as a unit, and the whole unit can be moved relative to obtain an image of the piece of U235.

To understand some exemplary methods for analyzing the data collected in embodiments of the invention, consider FIGS. 3A through 4B. In FIG. 3A, the MEGa-ray, which is tuned to a U235 NRF line, passes through the container without encountering any U235. If the beam was not tuned to either the U235 or the U238 NRF line, the amount of signal collected by each integrating detector would be about the same. There would be some reduction in power by absorption and scattering as the beam propagates through the first foil. Therefore, the two signals are normalized. If the beam is then tuned to a NRF line of U235, the difference between the signal levels in each detector is produced by the NRF from the U235 content of the first foil. This difference will not change if the entire container is removed. This is significant in one respect because the detection system can be set up and aligned and then targets, such as shipping containers, can be moved into the beam path. If the beam path does intersect material having U235 content, then the signal difference will be determined by the amount of U235 through which the beam passes. Placing this difference on a logarithmic scale will reveal small changes in the amount of U235 NRF produced signal collected by the integrating detector proximate to the U235 foil. This enables a variety of data analysis methods of varying degree of precision. For example, simply measuring the amount of signal collected by the U235 detector on resonance before and during interaction with a U235 target will show a signal difference that is dependent on the amount of U235 encountered. In another example, as discussed supra, a measurement is made of the amount of signal collected by the U235 detector and the U238 detector, on resonance, before and during interaction with a U235 target. The signals can first be normalized a variety of ways, including the substitution of a U238 foil for the U235 foil, or by tuning the MEGa-ray beam to be off resonance. The difference between the two signals on the U235 resonance is dependent on the amount of U235 encountered. In another method, a difference is determined between (i) the ratio of the U235 detector signal to the third detector and (ii) the ratio of the U238 detector signal to the third detector. In each method, depiction of the results on a log scale reveals much smaller changes than on a linear scale. Other signal analysis methods will now be apparent to those skilled in the art based on these examples.

Variations and uses of the invention will now be apparent to those skilled in the art. For example, the techniques disclosed here can be used for materials other than the ones disclosed. Other configurations of integrating detectors can be employed within the scope of this invention. Embodiments of the invention can be used to rapidly determine the isotope content of moving targets such as those as to be used in the Laser Inertial Fusion-Fission Energy (LIFE) Project at the Lawrence Livermore National Laboratory or in a pebble bed reactor. If cases where the object is moving, configurations of the invention are usable to measure the Doppler shift for determination of velocities The foregoing description of the invention has been presented for purposes of illustration and description and is not intended to be exhaustive or to limit the invention to the precise form disclosed. U.S. Provisional Application No. 60/720,965 is incorporated herein by reference. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. An apparatus, comprising:
    a first structure;
    a first integrating detector operatively positioned to detect a signal A from said first structure;
    a second structure; and
    a second integrating detector operatively positioned to detect a signal B from said second structure, wherein said first structure and said second structure comprise the same atomic material, wherein said first structure comprises a portion A that consist essentially of a first isotope, wherein said second structure comprises a portion B that consists essentially of a second isotope, wherein said first structure and said second, structure are configured to intercept at least some portion of a mono-energetic gamma-ray (MEGa-ray) beam.

2. The apparatus of claim 1, further comprising a third integrating detector configured to intercept at least some portion of said mono-energetic gamma-ray (MEGa-ray) beam.

3. The apparatus of claim 1, further comprising a MEGa-ray source for providing said beam.

4. The apparatus of claim 3, wherein said source can be configured to provide said beam at a nuclear resonance fluorescence line (NRF) of one of said first isotope or said second isotope.

5. The apparatus of claim 2, wherein said source is configured to direct said beam to propagate through said first structure and said second structure and onto said third integrating detector.

6. The apparatus of claim 1, wherein said first structure comprises a first foil and wherein said second structure comprises a second foil.

7. The apparatus of claim 3, wherein said first structure is formed into a first part of a disk and wherein said second structure is formed into a second part of said disk, said apparatus further comprising means for rotating said disk wherein said beam can, at different times, pass through said first part and said second part.

8. The apparatus of claim 1, wherein said first isotope consists of U235 and wherein said second isotope consists of U238.

9. The apparatus of claim 1, wherein said signal A is selected from a first group consisting of photons and scatter and wherein said signal B is selected from a second group consisting of photons and scatter.

10. The apparatus of claim 3, wherein said source is capable of producing MEGa-ray energy of at least 1 MeV.

11. The apparatus of claim 1, further comprising means for providing relative movement between said beam and at least one of said first structure or said second structure.

12. The apparatus of claim 1, wherein each of said first integrating detector and said second integrating detector comprises a scintillator, at least one photomultiplier and a Compton shield.

13. The apparatus of claim 2, wherein said first structure is one of a plurality of first structures arranged in a first pixel group, wherein said second structure is one of a plurality of second structures arranged in a second pixel group, wherein said third integrating detector is one of a plurality of third integrating detectors.

14. The apparatus of claim 13, wherein each of said first pixel group, said second pixel group and said plurality of third integrating detectors are arranged in an array selected from the group consisting a one dimensional array and a two dimensional array.

15. The apparatus of claim 13, wherein at least a portion of each of said first pixel group, said second pixel group and said plurality of third integrating detectors are configured to intercept at least some portion of said MEGa-ray beam.

16. The apparatus of claim 2, further comprising means for analyzing at least one of said signal A, said signal B and a signal C from said third integrating detector to determine at least one of (i) the presence of an isotope and (ii) the amount of said isotope.

17. The apparatus of claim 2, further comprising means for analyzing at least one of said signal A, said signal B and a signal C from said third integrating detector to produce an image selected from the group consisting of a 2-D image and a 3D image.

18. A method, comprising:
    interacting a mono-energetic gamma-ray (MEGa-ray) beam with a test object, a first structure and a second structure, wherein said first structure and said second structure comprise the same atomic material, wherein said first structure comprises a portion A that consist essentially of a first isotope, wherein said second structure comprises a portion B that consists essentially of a second isotope;
    detecting a first portion of scatter and photons resulting from the interaction of said MEGa-ray beam with said first structure to produce a signal A;
    detecting a second portion of scatter and photons resulting from the interaction of said MEGa-ray beam with said second structure to produce a signal B; and
    comparing said signal A to said signal B to determine if said test object comprises one of said first isotope or said second isotope.

19. The method of claim 18, further comprising comparing said signal A to said signal B to determine the amount of one of said first isotope or said second isotope present in said test object.

20. The method of claim 18, further comprising detecting, with a beam monitor, the energy in said beam, wherein the step of detecting detects energy after said beam interacts with said test object, said first structure and said second structure, to produce a signal C.

21. The method of claim 20, further comprising determining the assay of said specific material.

22. The method of claim 21, wherein the step of determining the assay of said specific material comprises:
    calculating a ratio A of said signal A to said signal C;
    calculating a ratio B of said signal B to said signal C; and
    calculating a difference between said ratio A and said ratio B.

23. The method of claim 22, further comprising plotting said difference on a logarithmic scale.

24. The method of claim 18, wherein said MEGa-ray comprises an energy of at least 1 MeV.

25. The method of claim 18, further comprising providing relative movement between said beam and at least one of said first structure or said second structure.

26. The method of claim 18, wherein said first structure is one of a plurality of first structures arranged in a first pixel group, wherein said second structure is one of a plurality of second structures arranged in a second pixel group, wherein said beam monitor is one of a plurality of beam monitors.

27. The method of claim 26, wherein each of said first pixel group, said second pixel group and said plurality of beam monitors are arranged in an array selected from the group consisting a one dimensional array and a two dimensional array.

28. The method of claim 26, wherein at least a portion of each of said first pixel group, said second pixel group and said plurality of beam monitors are configured to intercept at least some portion of said MEGa-ray beam.

29. The method of claim 20, further comprising analyzing at least one of said signal A, said signal B and a signal C to produce an image selected from the group consisting of a 2-D image and a 3D image.

* * * * *